United States Patent [19]

Seki et al.

[11] 4,175,185
[45] Nov. 20, 1979

[54] PROCESS FOR PREPARING CEPHALOSPORANIC ACID DERIVATIVES

[75] Inventors: Shigeo Seki, Tokyo; Satoru Nakabayashi; Toshinori Saito, both of Yokohama; Shunzō Fukatsu, Tokyo; Shokichi Nakajima, Yokohama; Toshiyasu Ishimaru, Suita, all of Japan

[73] Assignee: Meiji Seika Kaisha Ltd., Tokyo, Japan

[21] Appl. No.: 892,179

[22] Filed: Mar. 31, 1978

Related U.S. Application Data

[63] Continuation-in-part of Ser. No. 792,799, May 2, 1977, abandoned.

[30] Foreign Application Priority Data

May 19, 1976 [JP] Japan .................................. 51/56645

[51] Int. Cl.$^2$ ............................................ C07D 501/20
[52] U.S. Cl. ........................................ 544/28; 544/30
[58] Field of Search ................................... 544/30, 28

[56] References Cited

U.S. PATENT DOCUMENTS

| | | | |
|---|---|---|---|
| 4,022,773 | 5/1977 | Ishimaru | 544/30 |
| 4,074,047 | 2/1978 | Foxtun et al. | 544/30 |
| 4,079,180 | 3/1978 | Susuki et al. | 544/30 |

*Primary Examiner*—Nicholas S. Rizzo
*Attorney, Agent, or Firm*—Frishauf, Holtz, Goodman & Woodward

[57] ABSTRACT

A process for preparing a cephalosporanic acid derivative or a 7-acylaminocephalosporanic acid derivative which comprises subjecting an esterifying agent to reaction in liquid sulfur dioxide in the presence of a base with an N-protected-cephalosporin C to obtain a diester, subjecting the diester to reaction in an inert solvent with an iminohalide forming agent to produce an iminohalide, subjecting the iminohalide with a lower alcohol to produce an iminoether, subjecting the product produced, after subjecting the iminoether to reaction with a reactive derivative of an organic acid, to hydrolysis and further eliminating the ester group of the carboxylic acid.

16 Claims, No Drawings

PROCESS FOR PREPARING CEPHALOSPORANIC ACID DERIVATIVES

RELATED APPLICATION

This application is a continuation-in-part of our application Ser. No. 792,799, filed May 2, 1977, and now abandoned.

The present invention relates to a process for preparing a cephalosporanic acid derivative possessing antibacterial activity. More specifically, the present invention relates to a novel and efficient process for preparing a 7-acylaminocephalosporanic acid.

We have developed a novel and efficient process for preparing cephalosporin antibiotics which have conventionally been useful as pharmaceuticals. The conventional process for preparing a 7-acylaminocephalosporanic acid is as follows. Namely, it is a process in which cephalosporin C is deacylated to produce 7-aminocephalosporanic acid (abbreviated as 7-ACA hereinafter) and then a reactive derivative of a carboxylic acid is reacted with 7-ACA. According to the process, 7-ACA, an intermediate, must be isolated at once and therefore there exist some defects in that the process becomes complicated and the yield decreases.

As a result of various investigations for overcoming these defects, we have found a process which is capable of preparing successively the desired 7-acylaminocephalosporanic acid in high yield by a simple procedure without producing 7-ACA as an intermediate.

Namely, an object of the present invention is to provide a process for preparing a cephalosporanic acid derivative of value for pharmaceuticals and having the formula (V):

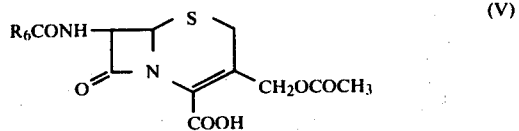

wherein $R_6CO$ represents an acyl group, which comprises producing a cephalosporin C derivative having the following formula (I) in which an amino group on the side chain is protected:

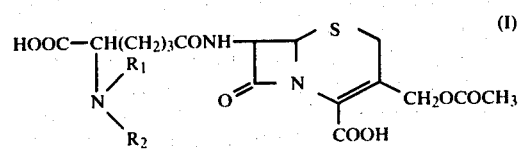

wherein $R_1$ represents a protective group for an amino group, and $R_2$ represents a hydrogen atom or a protective group for an amino group, or may form a ring structure together with $R_1$,
by a known method starting from cephalosporin C obtainable from nature,
subjecting the thus-produced compound (I) to reaction in liquid sulfur dioxide in the presence of a base with an esterifying agent having the formula (II):

wherein $R_3$, $R_4$ and $R_5$ may be the same or different, each represents a hydrogen atom, an alkyl group, a substituted or unsubstituted aryl group, an aralkyloxy group, an aralkylthio group, an aroyl group, an alkanoyloxy group, an aroyloxy group and an aroylamino group, and X represents a halogen atom or an organic sulfonyloxy group,
to obtain a diester having the formula (III):

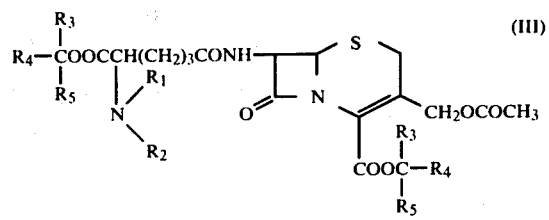

subjecting the diester (III) to reaction in an inert solvent with an iminohalide forming agent to produce an iminohalide, subjecting the iminohalide with a lower alcohol to produce an iminoether, subjecting the product produced after subjecting the iminoether to reaction with a reactive derivative of an organic acid having the formula (IV):

$$R_6—COOH \quad (IV)$$

wherein $R_6CO$ represents an acyl group, to hydrolysis, and further eliminating the ester group of the carboxylic acid.

Conventionally, when an amido group in a cephalosporin compound is converted into an iminohalide group or an iminoether group, the carboxylic acid at the 4-position must be protected. For the purpose, silylation and esterification have been known.

The silylating method is not a desirable method industrially, since silylating agents are expensive and conversion of an amido group in a silyl derivative of cephalosporin C into an iminohalide group and an iminoether group must be conducted at a low temperature of $-50°\sim -40°$ C. in order to prevent the elimination of the protective silyl group (Japanese Patent Publication Sho-49-45878/1974).

When an ester which is more stable than a silyl derivative is used, the reaction need not be conducted at such a low temperature. However, when esterification is conducted in the presence of a base by using an alkyl halide, etc., a part or the greater part of a $\Delta^3$-cephalosporin ester isomerizes into a $\Delta^2$-cephalosporin ester in the course of the reaction. In this case, in order to turn the $\Delta^2$-ester back to the $\Delta^3$-ester, the isomeric mixture may be oxidized with a peroxide such as m-chloroperbenzoic acid, etc., and then reduced with phosphorus trichloride, etc. (*Cephalosporins and Penicillins Chemistry and Biology* by E. H. Flynn, pp. 147–151), or separation and purification may necessarily be conducted by column chromatography to isolate the $\Delta^3$-ester.

Recently, there has been known a method in which an equivalent amount of a base is added to an equimolar mixture of cephalosporin and a halomethyl ester under such a rate that the generation rate of an acid anion becomes equal to that of the ester to prevent the side-reaction producing the $\Delta^2$-ester (Japanese Provisional Patent Publication Sho-51-16687/1976). However, all of these methods mentioned above are complicated in their procedures and are characterized by low yields.

As other esterifying methods, there exist a method in which a diazoalkane is used, a method in which a dehydrating agent such as dicyclohexylcarbodiimide, etc., is used, and so on. These methods, however, cannot be applied industrially since the reagents employed are very expensive.

As described above, conventional techniques do not provide industrially and easily a $\Delta^3$-cephalosporin ester in good yields.

As a result of various investigations concerning esterifying methods which do not cause isomerization of a double bond, we have found an entirely novel process in which esterification is conducted in liquid sulfur dioxide.

The process of the present invention is explained below in order of the progress of work.

The present invention is carried out first by dissolving an N-protected-cephalosporin C having the formula (I) and an esterifying agent having the formula (II) in liquid sulfur dioxide and refluxing the resulting mixture at a temperature of $-10° \sim -5°$ C. for several hours in the presence of a base.

As $R_1$, a protective group for an amino group of cephalosporin C, there is: a $C_2$-$C_4$ alkanoyl group such as an acetyl group, a propionyl group, a butyryl group; an aroyl group such as a benzoyl group, a p-chlorobenzoyl group, a p-nitrobenzoyl group, etc.; a $C_1$-$C_5$ alkoxycarbonyl group such as an ethoxycarbonyl, t-butoxycarbonyl, t-amyloxycarbonyl group, etc.; a $C_1$-$C_4$ haloalkoxycarbonyl group such as a 2-chloroethoxycarbonyl, 2-bromoethoxycarbonyl group, etc.; a ($C_1$-$C_4$)alkoxy-($C_1$-$C_4$)alkoxycarbonyl group such as a 2-methoxyethoxycarbonyl, 2-(n-butoxy)ethoxycarbonyl group, etc.; an aralkoxycarbonyl group such as a benzyloxycarbonyl and a $C_1$-$C_2$alkoxybenzyloxycarbonyl illustrated by p-methoxybenzyloxycarbonyl and p-ethoxybenzyloxycarbonyl; p-chlorobenzyloxycarbonyl group; a substituted aryl group such as a 2,4-dinitrophenyl, 2,4,6-trinitrophenyl, 2,4-dinitro-6-methoxyphenyl, 4-cyanophenyl, 4-carbomethoxyphenyl group, etc.; an arylsulfonyl group such as a benzenesulfonyl, tosyl group, etc.; and an arylsulfenyl group such as a o-nitrophenylsulfenyl group, etc.

For the ring structure formed by $R_1$ and $R_2$, there may be mentioned a phthaloyl, tetrabromophthaloyl, tetrachlorophthaloyl group and so on.

As an esterifying agent having the formula (II), any agent for esterifying a carboxylic acid may be used if the ester produced suffers elimination under mild conditions. As representative examples for

having such properties, there may be mentioned the following: alkyl groups having from 1 to 4 carbon atoms such as t-butyl, benzyl and substituted benzyl such as p-nitrophenylmethyl, benzhydryl, di(p-nitro)-benzhydryl, di-(p-methoxy)benzhydryl, benzyloxymethyl, benzylthiomethyl, phenacyl, ($C_1$-$C_4$)alkanoyloxymethyl such as acetoxymethyl and pivaloyloxymethyl, benzoxymethyl, α-benzoyloxyethyl group, etc. As X may be mentioned, a halogen atom such as a chlorine, bromine, iodine atom, etc., and a sulfonyloxy group such as a methanesulfonyloxy, benzenesulfonyloxy, p-toluenesulfonyloxy group, etc.

As bases employed, there may be mentioned a tertiary or secondary amine, for example, triethylamine, tripropylamine, tributylamine, pyridine, picoline, lutidine, collidine, quinoline, isoquinoline, N-methylmorpholine, N-ethylmorpholine, N-methylpiperidine, N-ethylpiperidine, N-methylpyrrolidine, N-ethylpyrrolidine, N,N'-tetramethylguanidine, diethylamine, monomethylaniline, piperidine, pyrrolidine, N,N-dimethylaniline, N,N-diethylaniline, etc.

The product thus obtained by the present process does not contain a $\Delta^2$-cephalosporin ester at all.

Accordingly, the complicated procedures such as turning back of the by-product $\Delta^2$-ester to the $\Delta^3$-ester or separation and purification by column chromatography, etc., which are necessary in the conventional methods mentioned above, are not required in the present process. The $\Delta^3$-ester obtained by the present process is stable and can be purified easily by recrystallization. The thus-purified product can be provided for the subsequent reaction. When the ester of the present invention is used, the subsequently conducted iminohalide and iminoether forming reactions can be carried out under temperature conditions (at a temperature of $-10°\sim 0°$ C.) which can be kept with ease industrially, while the conventional silyl derivatives necessitate a low temperature of $-40°\sim -50°$ C. for the purpose. Hence, the present process does not necessitate special equipment to maintain a low temperature.

Thus, the present process is suitable for industrial manufacture since it is not only far superior to conventional processes from the standpoints of yield and procedure, but also liquid sulfur dioxide used as a material in the present process is inexpensive.

Next, the $\Delta^3$-cephalosporin ester is dissolved in an anhydrous inert solvent such as dichloromethane, chloroform, etc., and converted into an iminohalide by reaction with an iminohalide forming agent at $-10°\sim 0°$ C. in the presence of a tertiary amine such as pyridine, N,N-dimethylaniline, etc. As the iminohalide forming agents, phosphorus trichloride, phosphorus pentachloride, phosphorus tribromide, phosphorus pentabromide, phosphoryl chloride, phosphoryl bromide, etc., may be used. As the lower alcohols ($C_1$-$C_4$), methanol, ethanol, propanol, butanol, etc., may widely be used.

Then, a reactive derivative of a carboxylic acid having the general formula (IV) is reacted. As the carboxylic acids, there may be exemplified the following:

Phenylacetic acid derivatives such as α-chloro-α-phenylacetic acid, α-bromo-α-phenylacetic acid, α-azido-α-phenylacetic acid, α-acetoxy-α-phenylacetic acid, α-propionyloxy-α-phenylacetic acid, α-benzoyloxy-α-(2-thienyl)acetic acid, α-t-butyloxy-α-(p-methoxyphenyl)acetic acid, α-valeryloxy-α-(p-nitrophenyl)acetic acid, α-t-amyloxycarbonyloxy-α-phenylacetic acid, α-t-butyloxycarbonyloxy-α-phenylacetic acid α-(2',2',2'-trichloroacetoxy)-α-phenylacetic acid, α-(β-halogenoethoxycarbonyloxy)-α-(2-thienyl)acetic acid, α-(2'-phenylacetoxy)-α-phenylacetic acid, α-benzyloxycarbonyloxy-α-phenylacetic acid, α-(p-halogenophenoxyacetoxy)-α-phenylacetic acid, α-[N-(2,2,2-trichloroethoxycarbony)amino]-α-phenylacetic acid, α-[N-(benzyloxycarbonyl)amino]-α-phenylacetic acid, α-[N-(t-butoxycarbonyl)amino]-α-phenylacetic acid, α-[N-(t-amyloxycarbonyl)amino]-α-phenylacetic acid, α-[N-(o-nitrobenzyloxycarbonyl)amino]-α-phenylacetic acid, α-[N-(p-nitrobenzyloxycarbonyl)amino]-α-phenylacetic acid, α-N-(1-carbamylpropen-2-yl)amino]-α-phenylacetic acid, α-methylthio-α-phenylacetic acid, α-ethoxycarbony-α-phenylacetic acid, α-2-thienylacetic acid, α-(p-nitrobenzyloxy)-α-(2-thienyl)acetic acid, mandelic acid, pyridylmercaptoacetic acid, tetrazolylacetic acid, 1-aminocyclohexanecarboxylic acid, α-aminocyclohexadienylacetic acid, α-aminocyclohexenylacetic acid, cyanoacetic acid, etc.

As the reactive derivatives of a carboxylic acid, an alkali metal salt of a mixed anhydride derived from an organic acid and anhydrous sulfuric acid (sulfur trioxide) [Japanese Patent Appln. No. Sho-49-20421/1974], and known functional derivatives such as an acid halide, acid anhydride, mixed acid anhydride, active ester, acid azide, acid cyanide, active acid amide, etc., may be used. At this time, it is preferable to have an organic base present in the medium. As the organic base to be used then, tertiary amines such as pyridine, N,N-dimethylaniline, etc., are preferably used. The reaction temperature is not critical. However, it is preferable to conduct the reaction between −10° C. and room temperature. The thus-obtained reaction product is poured into water to effect hydrolysis. The reaction proceeds readily between an ice-cooled temperature and room temperature so that an acyl group on the 7-amino group is exchanged. The hydrolysis is preferably conducted by using an acid or a base. When an acid is used, it is preferable to maintain the pH value of the medium between 1.5 and 2.5. The esterified 7-acylaminocephalosporanic acid thus obtained is isolated and purified according to an ordinary method. The ester group is eliminated finally. The elimination of ester group is effected under ordinary mild conditions. In the case of a benzhydryl ester, for example, the use of trifluoroacetic acid can give a 7-acylaminocephalosporanic acid in high yield. For the 7-acylaminocephalosporanic acid obtained as a desired product according to the present invention and represented by the formula (V), there may be exemplified 7-acylaminocephalosporanic acids which may be acylated by using various kinds of carboxylic acids (IV). Representative examples for the 7-acylaminocephalosporanic acids are 7-(2-thienylacetamido)cephalosporanic acid, 7-(α-4-pyridylthioacetamido)cephalosporanic acid, 7-cyanoacetamidocephalosporanic acid, 7-(α-aminophenylacetamido)cephalosporanic acid, etc.

As described above in detail, the present invention provides a process for obtaining a desired 7-acylaminocephalosporanic acid, which process comprises protecting the carboxyl group of an N-protected-cephalosporin C by esterifying said cephalosporin C in liquid sulfur dioxide without rearrangement of the double bond therein, producing an iminochloride and then an iminoether, and subsequently exchanging acyl groups by using a reactive derivative of a suitable organic acid. The present process has advantageous points of extreme industrial excellence as follows:

(i) The yield of the present process is higher than that of a conventional method;
(ii) The procedures are simple;
(iii) The reagents employed are easily available economically;
(iv) Hence, the desired product can be manufactured at low cost.

The present invention is explained more in detail by the following non-limiting examples.

EXAMPLE 1

Preparation of dibenzhydryl ester of N-phthaloylcephalosporin C (A) Preparation of N-phthaloylcephalosporin C To 80 ml. of an aqueous solution containing 4.4 g. (10 m. mol) of cephalosporin C were added 3.5 g. of sodium bicarbonate to adjust the pH value to 7.0–7.3. To the resulting solution were added 35 ml. of acetone. Then, 50 ml. of an acetone solution containing 3 g. of N-carbethoxyphthalimide were added dropwise while stirring. After the dropwise addition, the mixture which formed was stirred at 20° C. for 1.5 hours. Then the mixture was diluted with 150 ml. of water and the thus-obtained solution was washed twice with 100 ml. of ethyl acetate. After adjusting the pH value of the aqueous solution to 2 by using 2 N hydrochloric acid, the solution was extracted three times with 100 ml. of ethyl acetate. The extract was dried over magnesium sulfate and the solvent was removed by evaporation to obtain an oil of N-phthaloylcephalosporin C.

(B) Preparation of N-phthaloylcephalosporin C benzhydryl ester

In 50 ml. of liquid sulfur dioxide were dissolved 5.78 g. of N-phthaloylcephalosporin C obtained in (A) and 6.05 g. (30 mmol) of α-chlorodiphenylmethane. Under gentle reflux at −5° C. of the resulting mixture, 3.5 ml. (25 mmol) of triethylamine were added dropwise over 10 minutes. After addition thereof and further reflux for 4.5 hours, liquid sulfur dioxide was removed by evaporation to obtain an oily substance. This substance was dissolved in chloroform to obtain 200 ml. of solution, which was then washed with water under acidic conditions, and successively with a saturated aqueous solution of sodium bicarbonate and a saturated aqueous solution of sodium chloride. The chloroform layer which was obtained was dried over anhydrous magnesium sulfate and evaporated to dryness by removing chloroform. The resulting solid residue was crystallized from ethyl acetate to obtain 4.65 g. of the diester. Single spot was observed on TLC. NMR shows only the existence of $\Delta^3$-ester.

Elementary analysis (%) ($C_{50}H_{43}N_3O_{10}S = 873.33$)

|  | C | H | N | S |
|---|---|---|---|---|
| Calculated | 68.31 | 4.93 | 4.90 | 3.65 |
| Found | 68.15 | 4.99 | 4.96 | 3.70 |

NME spectrum (CDCl$_3$, 100 MHz), ppm (Hz): 1.66/2.23 (—CH$_2$CH$_2$CH$_2$—, m), 1.93 (CH$_3$CO—, s), 3.16/3.36 (—SCH$_2$—, AB, J=18.5), 4.69/4.95 (—CH$_2$O—, A/B, J=14), 4.83 (H-6, d, J=5), 4.91 (thien CH, t, J=6.5), 5.73 (H-7, dd, J=8.5, 5), 6.58 (—NH—, d, J=8.5), 6.85 (ester —OCH<, s), 7.15/7.21/7.28 (20 arom H, m), 7.67, 7.33 (4 arom H, m).

EXAMPLE 2

Preparation of N-phthaloylcephalosporin C dibenzhydryl ester

Starting from an aqueous solution containing 4.4 g. of cephalosporin C, an oil of N-phthaloylcephalosporin C was obtained according to the procedure (A) in Example 1. Next, 9.88 g. of α-bromodiphenylmethane were reacted as an esterifying agent with the thus-obtained oil to obtain 7.1 g. of N-phthaloylcephalosporin C dibenzhydryl ester. The substance showed a single spot on TLC. NMR spectrum thereof showed only the existence of $\Delta^3$-ester.

EXAMPLE 3

Preparation of cephalothin dibenzhydryl ester

In 20 ml. of anhydrous dichloromethane were dissolved 1.76 g. of N-phthaloyl cephalosporin C dibenzhydryl ester.

After cooling the solution to $-10°$ C., 0.500 g. of phosphorus pentachloride and then 0.261 g. of pyridine were added and the resulting mixture was stirred at that temperature for 1 hour and then at $0 \sim -5°$ C. for 1 hour. After 10 ml. of anhydrous methanol had been added to the resulting mixture at $-10°$ C., the mixture which formed was stirred at the same temperature for one hour and then at $0°$ to $-5°$ C. for one hour. The reaction mixture was cooled to $-10°$ C. and 3.03 g. of N,N-dimethylaniline were added to the mixture. Next, an N,N-dimethylformamide solution containing 4 mmol of sodium salt of mixed anhydride of 2-thienylacetic acid and sulfur trioxide was added and the mixture was stirred for 2 hours at $0 \sim -5°$ C. The reaction mixture was poured into ice water and stirred for 1 hour under ice cooling at a pH value of $1.5 \sim 2.0$. The mixture was then extracted with chloroform and washed with water.

After removing the solvent by evaporation in vacuo, dissolving the residue in 20 ml. of ethyl acetate and washing the solution with a saturated aqueous solution of sodium bicarbonate and with water, the thus-treated solution was dried over anhydrous magnesium sulfate. The solvent was removed by evaporation in vacuo and the residue was chromatographed on a column of silica gel to develop and elute a main product with chloroform. The solvent was removed from the eluate by evaporation to obtain 0.89 g. of cephalothin {7-(2-thienylacetamido)cephalosporanic acid dibenzhydryl ester}. The IR and NMR spectra of the product were identical entirely with those of an authentic sample, respectively. Elementary analysis (%) ($C_{29}H_{26}N_2O_6S_2 = 562.69$)

|  | C | H | N | S |
|---|---|---|---|---|
| Calculated | 69.90 | 4.66 | 4.98 | 11.40 |
| Found | 70.05 | 4.70 | 4.6 | 11.42 |

NMR spectrum (CDCl$_3$, 60 MHz), ppm (Hz): 2.00 (CH$_3$CO—, s), 3.35/3.40 (—SCH$_2$—, AB, J=18), 3.82 ( 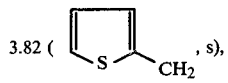 , s), 4.79/5.01 (—CH$_2$O—, AB, J=15), 4.89 (H-6, d, J=5), 5.79 (H-7, dd, J=9.5, 5), 6.77 (NH, d, J=9.5), 6.91 (ester —OCH<, s).

EXAMPLE 4

Preparation of cephalothin dibenzhydryl ester

In 20 ml. of anhydrous dichloromethane were dissolved 1.76 g. of N-phthaloylcephalosporin C dibenzhydryl ester.

After cooling the solution to $-10°$ C., 0.500 g. of phosphorus pentachloride was added thereto. After adding subsequently 0.261 g. of pyridine, the mixture was stirred at that temperature for 1 hour and at $0 \sim -5°$ C. for 1 hour. After 10 ml. of anhydrous methanol had been added thereto at $-10°$ C., the mixture which formed was stirred at the same temperature for one hour and then at $0°$ to $-5°$ C. for one hour. After cooling the reaction mixture to $-10°$ C., 3.03 g. of N,N-dimethylaniline and then 0.67 g. of 2-thienylacetyl chloride were added and the resulting mixture was stirred for 2 hours at $0 \sim -5°$ C. The resulting mixture was poured into 30 ml. of ice water and stirred at a pH value of $1.5 \sim 2.0$ under ice-cooling for 1 hour. After extraction with chloroform, the extract was washed with water. After removing the solvent by evaporation in vacuo, dissolving the residue in 20 ml. of ethyl acetate, and washing with a saturated aqueous solution of sodium bicarbonate and with water, the solution was dried over anhydrous magnesium sulfate. After removing the solvent by evaporation in vacuo, the residue was chromatographed through a column of silica gel to develop and elute the main product. After removing the solvent from the eluate by evaporation, 0.84 g. of cephalothin dibenzhydryl ester was obtained.

IR and NMR spectra of the product were entirely identical with those of an authentic sample, respectively.

EXAMPLE 5

Preparation of cephalothin

In 5 ml. of anisole was dissolved 0.563 g. of cephalothin benzhydryl ester. After adding 20 ml. of trifluoroacetic acid and stirring the mixture at $5 \sim 15°$ C. for 5 minutes, the mixture was concentrated under reduced pressure. The thus-produced residue was dissolved in ethyl acetate and washed with water. After drying over anhydrous magnesium sulfate and removing the solvent by evaporation in vacuo, ether was added to the mixture to crystallize and obtain cephalothin.

IR and NMR spectra of the product were entirely identical with those of an authentic sample, respectively.

EXAMPLE 6

Preparation of N-benzoylcephalosporin C benzhydryl ester (A) Preparation of N-benzoylcephalosporin C To 100 ml. of an aqueous solution containing 4.15 g. (40 mmol) was added a saturated aqueous solution of sodium hydrogen carbonate to adjust to a pH of from 7.0 to 7.3. 100 ml. of acetone were added to the mixture and 2.1 g. (15 mmol) of benzoylchloride in 21 ml. of acetone were added dropwise with stirring under ice-cooling. Then, the reaction mixture was stirred further for one hour at the same temperature. An aqueous solution of sodium hydrogen carbonate was added during the reaction to keep pH at 7.0~7.3.

After acetone was distilled off under reduced pressure, the resulting residue was washed twice with 10 ml. portions of ethyl acetate. The water layer was adjusted to pH 3.3 and washed twice with 20 ml. portions of benzene and, after being adjusted to pH 2.0, was extracted three times with 20 ml. portions of benzene. The extract was dried over magnesium sulfate and distilled off to give 4.38 g. of N-benzoylcephalosporin C in a yield of 84.3%.

(B) Preparation of N-benzoylcephalosporin C dibenzhydryl ester

The oil-containing 10 mmol of N-benzoylcephalosporin C obtained above and 6.05 g. (30 mmol) of α-chlorodiphenylmethane were dissolved in 100 ml. of liquid sulfur dioxide, and the resulting mixture was gently refluxed at −5° C. 3.5 ml. (25 mmol) of triethylamine were added dropwise over 10 minutes under reflux. After the addition, the mixture was refluxed for 5.5 hours and the liquid sulfur dioxide was removed by evaporation, whereupon an oil was obtained. This oil was dissolved in 200 ml. of ethyl acetate and washed with an acidic water to remove basic compounds, and then washed successively with a saturated aqueous solution of sodium hydrogen carbonate and a saturated aqueous solution of sodium chloride.

The ethyl acetate solution was dried over magnesium sulfate and evaporated to dryness to give a solid, which was then washed with ether; 1.11 g. of the diester were obtained. This solid showed a single spot by thin layer chromatography and NMR spectrum did not show the presence of $\Delta^2$-compound.

EXAMPLE 7

Preparation of cephalothin benzhydryl ester 1.70 g. (2 mmol) of N-benzoylcephalosporin C dibenzhydryl ester obtained in Example 6 were dissolved in 20 ml. of anhydrous dichloromethane and cooled to −10° C. 0.500 g. of phosphorus pentachloride and 0.261 g. of pyridine were added to the mixture, which was stirred at the same temperature for one hour and at 0° to −5° C. for one hour. The mixture was again cooled to −10° C. 1.98 g. of pyridine and 0.67 g. of thienylacetyl chloride were added and the mixture was stirred at 0° to −5° C. for 2 hours. The reaction mixture was poured into 30 ml. of ice-waater and stirred at pH 1.5 to 2.0 for one hour under ice-cooling and extracted with chloroform. The extract was washed with water and distilled under reduced pressure. The resulting residue was dissolved in 20 ml. of ethyl acetate and washed with a saturated sodium hydrogen carbonate and water and then dried over magnesium sulfate. The solvent was distilled off under reduced pressure and the residue which was obtained was subjected to silica gel column chromatography. The main product was developed and eluted with chloroform, and the eluate was distilled to obtain 0.82 g. of cephalothin benzhydryl ester.

EXAMPLE 8

Preparation of cephalothin benzhydryl ester 4.25 g. (5 mmol) of N-benzoylcephalosporin C dibenzhydryl ester obtained in Example 6 were dissolved in 50 ml. of dried dichloromethane and 1.56 g. of phosphorous pentachloride were added to the mixture at −13° C., and then 0.711 g. of pyridine was added. The mixture was stirred at the same temperature for one hour and at 0° to −5° C. for one hour. Then, 30 ml. of anhydrous methanol were added thereto at −10° C. and the mixture was stirred at the same temperature for one hour and at 0° to −5° C. for one hour. 5.53 g. of pyridine were added thereto while keeping the temperature at −10° C., and then a dimethylformamide solution of thienylacetic acid-anhydrous sulfuric acid mixed anhydride sodium salt corresponding to 10 mmol was added thereto and the mixture was stirred at 0° to −5° C. for two hours.

The reaction mixture was poured into 80 ml. of ice-water and stirred at pH 1.5 to 2.0 for one hour under ice-cooling. The mixture was extracted with chloroform and washed with water. The extract was distilled off under reduced pressure and the resulting residue was dissolved in 60 ml. of ethyl acetate and washed twice with water and adjusted to pH 8.0 by adding an aqueous saturated solution of sodium hydrogen carbonate and further washed twice with 20 ml. portions of water. The ethyl acetate solution was dried over magnesium sulfate and distilled under reduced pressure.

The residue was subjected to silica gel column chromatography and the main product was developed and eluted with chloroform.

The eluate was distilled to give 2.20 g. of cephalothin benzhydryl ester.

REFERENTIAL EXAMPLE

An N,N-dimethylformamide solution containing sodium salt of mixed anhydride of 2-thienylacetic acid and sulfur trioxide was prepared according to the following procedure.

5 ml. of dimethylformamide were cooled to 0~10° C. While distilling sulfur trioxide, 0.4 g. thereof was blown into the solvent with stirring. After stirring the solution for 1.5 hours at that temperature, 0.656 g. of sodium salt of 2-thienylacetic acid was added and the mixture was stirred at 5°~15° C. for 1.5 hours to give an entirely transparent solution, thus yielding an N,N-dimethylformamide solution of sodium salt of mixed anhydride of 2-thienylacetic acid and sulfur trioxide.

As indicated above, the acyl groups $R_6CO$ include the following:

α-2-thienylacetyl,
α-(benzoyloxy)-α-(2-thienyl)acetyl,
α-(β-halogenoethoxycarbonyl)-α-(2-thienyl)acetyl,
α-(p-nitrobenzyloxy)-α-(2-thienyl(acetyl,
α-chloro-α-phenylacetyl,
α-bromo-α-phenylacetyl,
α-azido-α-phenylacetyl,
α-hydroxy-α-phenylacetyl,
α-acetoxy-αphenylacetyl,
α-propionyloxy-α-phenylacetyl,
α-t-amyloxycarbonyloxy-α-phenylacetyl,
α-t-butyloxycarbonyloxy-α-phenylacetyl,
α-(2,2,2-trichloroacetoxy)-α-phenylacetyl,
α-benzyloxy-α-phenylacetyl,
α-benzyloxycarbonyloxy-α-phenylacetyl,
α-methylthio-α-phenylacetyl,
α-ethoxycarbonyl-α-phenylacetyl,
α-[N-(2,2,2-trichloroethoxycarbonyl)amino]-α-phenylacetyl,
α-[N-(benzyloxycarbonyl)amino]-α-phenylacetyl,
α-[N-(t-butoxycarbonyl)amino]-α-phenylacetyl,
α-[N-(t-amylcarbonyl)amino]-α-phenylacetyl, α-[N-(o-nitrobenzyloxycarbonyl)amino]-α-phenyla-
  cetyl,
α-[N-(p-nitrobenzyloxycarbonyl)amino]-α-phenyla-
  cetyl,
pyridylmercaptoacetyl,
tetrazolylacetyl,
1-aminocyclohexanecarbonyl,
α-amino-α-cyclohexadienylacetyl,
α-amino-α-cyclohexenylacetyl,
α-cyanoacetyl,
α-t-butyloxy-α-(p-methoxy-phenyl)acetyl,
α-valeryloxy-α-(p-nitrophenyl)acetyl,
α-phenylacetoxy-α-phenylacetyl, and
α-(p-halogenophenoxyacetoxy)-α-phenylacetyl.

Thus, R$_6$CO can be a 2-thienyl group; an α-substituted-2-thienylacetyl group wherein the substituent is a substituted or unsubstituted benzoyloxy group, a substituted or unsubstituted benzyloxy group, or a substituted or unsubstituted alkoxycarbonyloxy group having 2–3 carbon atoms; an α-substituted-α-phenylacetyl group wherein the substituent is halo such as chloro and bromo, azido, hydroxy, alkanoyloxy having 2 to 5 carbon atoms, alkoxycarbonyloxy having 2 to 6 carbon atoms, halogenoalkanoyl having 2 to 3 carbon atoms, benzyloxycarbonyloxy, alkylthio having 1 to 2 carbon atoms, or alkoxycarbonyl having 2 to 5 carbon atoms; a substituted or unsubstituted benzyloxycarbonylamino group; a substituted or unsubstituted alkoxycarbonylamino group having 2 to 6 carbon atoms; and a (carbamylalken-2-yl)amino group wherein the alken moiety has 2 to 3 carbon atoms.

Additional R$_6$CO groups are α-(t-butyloxy)-α-(p-methoxyphenyl)acetyl; α-valeryloxy-α-(p-nitrophenyl)acetyl; pyridylmercaptoacetyl; tetrazolylacetyl; aminocyclohexanecarbonyl; aminocyclohexadienylacetyl; aminocyclohexenylacetyl; and cyanoacetyl.

What is claimed is:

1. A process for preparing a cephalosporanic acid having the formula (V):

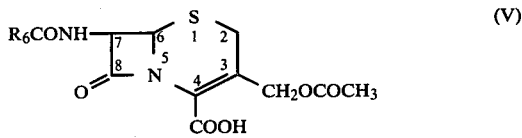

wherein R$_6$CO represents a 2-thienylacetyl group; an α-substituted-α-(2-thienyl)acetyl group wherein the substituent is a substituted or unsubstituted benzoyloxy group, a substituted or unsubstituted benzyloxy group, or a substituted or unsubstituted alkoxycarbonyloxy group having 2–3 carbon atoms; an α-substituted-α-phenylacetyl group wherein the substituent is halo, azido, hydroxy, alkanoyloxy having 2 to 5 carbon atoms, alkoxycarbonyloxy having 2 to 6 carbon atoms, halogenoalkanoyl having 2 to 3 carbon atoms, benzyloxycarbonyloxy, alkyltio having 1 to 2 carbon atoms, or alkoxycarbonyl having 2 to 5 carbon atoms; a substituted or unsubstituted benzyloxycarbonylamino group; a substituted or unsubstituted alkoxycarbonylamino group having 2 to 6 carbon atoms; a (carbamylalken-2-yl)amino group wherein the alken moiety has 2 to 3 carbon atoms; α-(t-butyloxy)-α-(p-methoxyphenyl)acetyl; α-valeryloxy-α-(p-nitrophenyl)acetyl; pyridylmercaptoacetyl; tetrazolylacetyl; aminocyclohex-anecarbonyl; aminocyclohexadienylacetyl; aminocyclohexenylacetyl and cyanoacetyl;

which comprises
contacting an esterifying agent having the formula (II):

wherein R$_3$, R$_4$ and R$_5$ may be the same or different, each represents a hydrogen atom, alkyl having from 1 to 4 carbon atoms, phenyl, nitrophenyl, methoxyphenyl, benzoyl, benzyloxy, benzylthio, (C$_1$–C$_4$)alkanoyloxy, benzoxy or benzoyloxy, and X represents a chlorine atom, a bromine atom, an iodine atom, methanesulfonyloxy, benzenesulfonyloxy or p-toluenesulfonoxy, in liquid sulfur dioxide in the presence of a secondary or tertiary amine selected from the group consisting of diethylamine, monomethylaniline, piperidine, pyrrolidine, N,N'-tetramethylguanidine, triethylamine, tripropylamine, tributylamine, pyridine, picoline, lutidine, collidine, quinoline, isoquinoline, N-methylmorpholine, N-ethylmorpholine, N-methylpiperidine, N-ethylpiperidine, N-methylpyrrolidine, N-ethylpyrrolidine, N,N-dimethylaniline and N,N-diethylaniline, at a temperature of from about −10° to about −5° C., with an N-protected-cephalosporin C having the formula (I):

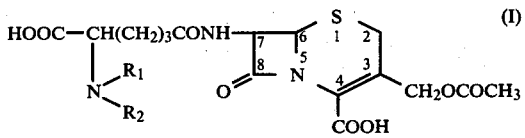

wherein R$_1$ represents a group selected from the group consisting of C$_1$–C$_4$ alkanoyl; benzoyl; nitrobenzoyl, halobenzoyl; C$_1$–C$_5$ alkoxycarbonyl; C$_1$–C$_4$ haloalkoxycarbonyl; (C$_1$–C$_4$)alkoxy-(C$_1$–C$_4$)alkoxycarbonyl; benzyloxycarbonyl; C$_1$–C$_2$ alkoxybenzyloxycarbonyl; halobenzyloxycarbonyl; phenyl substituted with nitro, methoxy, cyano or carbomethoxy; benzene sulfonyl; tosyl and nitrophenylsulfenyl; R$_2$ is hydrogen, or together with R$_1$ forms a ring selected from the group consisting of phthaloyl and halophthaloyl, to form a diester having the formula (III):

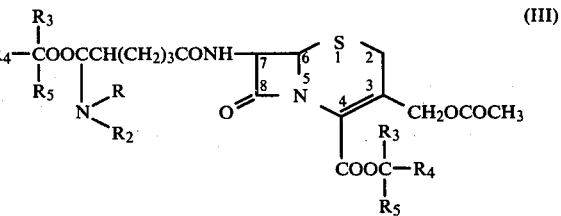

wherein R$_1$, R$_2$, R$_3$, R$_4$ and R$_5$ are as defined above,
contacting the diester (III) in an inert solvent with an iminohalide forming agent at a temperature of from about −10° to about 0° C. to form an iminohalide,
contacting the iminohalide with a lower alcohol having from 1 to 4 carbon atoms to form an iminoether, contacting the iminoether with an active derivative of an organic acid having the formula (IV):

$$R_6\text{—COOH} \qquad (IV)$$

wherein $R_6CO$ is as defined above;
said active derivative being selected from the group consisting of an alkali metal salt of a mixed anhydride of said organic acid and sulfur trioxide; and a halide, an anhydride, an active ester, an azide, a cyanide, and an amide of said organic acid, to form a reaction product,
hydrolyzing said reaction product, and
converting the ester group at the 4-position of the ring to a carboxylic acid group.

2. The process of claim 1, wherein the group $$\begin{array}{c}R_3\\ R_4\text{—C—}\\ R_5\end{array}$$

of said esterifying agent represents t-butyl, p-nitrophenylmethyl, benzhydryl, di-(p-nitro)benzhydryl, di-(p-methoxy)benzhydryl, benzyloxymethyl, benzylthiomethyl, phenacyl, acetoxymethyl, pivaloyloxymethyl, benzoxymethyl or α-benzoyloxyethyl.

3. The process of claim 1, wherein said ring formed of $R_1$ and $R_2$ is a phthaloyl group, a tetrachlorophthaloyl group or a tetrabromophthaloyl group.

4. The process of claim 1, wherein said iminohalide forming agent is a phosphorus halide or a phosphoryl halide.

5. The process of claim 1, wherein said lower alcohol is methyl alcohol.

6. The process of claim 1, wherein said material contacted with the iminoether is an alkali metal salt of a mixed anhydride of an organic acid and sulfur trioxide.

7. The process of claim 1, wherein said organic acid is a phenylacetic acid, thienylacetic acid, mandelic acid, pyridylmercaptoacetic acid, tetrazoylacetic acid, 1-amino-cyclohexanecarboxylic acid, α-aminocyclohexadienylacetic acid, α-amino-cyclohexenylacetic acid or cyanoacetic acid.

8. A process for preparing a cephalosporanic acid having the formula (V):

(V)

wherein $R_6CO$ is as defined above;
which comprises contacting an N-protected-cephalosporin C diester having the formula (III):

(III)

wherein $R_1$ represents a group selected from the group consisting of $C_1$-$C_4$ alkanoyl; benzoyl; nitrobenzoyl; halobenzoyl; $C_1$-$C_5$ alkoxycarbonyl; $C_1$-$C_4$ haloalkoxycarbonyl; ($C_1$-$C_4$)alkoxy-($C_1$-$C_4$)alkoxycarbonyl; benzyloxycarbonyl; $C_1$-$C_2$ alkoxybenzyloxycarbonyl; halobenzyloxycarbonyl; phenyl substituted with nitro, methoxy, cyano or carbomethoxy; benzene sulfonyl; tosyl and nitrophenylsulfenyl; $R_2$ is hydrogen, or together with $R_1$ forms a ring selected from the group consisting of phthaloyl and halophthaloyl,
in an inert solvent with an iminohalide forming agent at a temperature of from about −10° C. to about 0° C. to form an iminohalide,
contacting the iminohalide with a lower alcohol having from 1 to 4 carbon atoms to form an iminoether,
contacting the iminoether with an active derivative of an organic acid having the formula (IV):

$$R_6\text{—COOH} \qquad (IV)$$

wherein $R_6CO$ is as defined above;
said active derivative being selected from the group consisting of an alkali metal salt of a mixed anhydride of said organic acid and sulfur trioxide; and a halide, an anhydride, an active ster, an azide, a cyanide, and an amide of said organic acid, to form a reaction product,
hydrolyzing said reaction product, and
converting the ester group at the 4-position of the ring to a carboxylic acid group.

9. The process of claim 8, wherein the group $$\begin{array}{c}R_3\\ R_4\text{—C—}\\ R_5\end{array}$$

of said diethyl ester (III) represents t-butyl, p-nitrophenylmethyl, benzhydryl, di-(p-nitro)benzhydryl, di-(p-methoxy)benzhydryl, benzyloxymethyl, benzylthiomethyl, phenacyl, acetoxymethyl, pivaloyloxymethyl, benzoxymethyl, or α-benzoyloxyethyl.

10. The process of claim 8, wherein said ring formed of $R_1$ and $R_2$ is a phthaloyl group, a tetrachlorophthaloyl group or a tetrabromophthaloyl group.

11. The process of claim 8, wherein said iminohalide forming agent is a phosphorus halide or a phosphoryl halide.

12. The process of claim 8, wherein said lower alcohol is methyl alcohol.

13. The process of claim 8, wherein said material contacted with said iminoether is an alkali metal salt of a mixed anhydride of an organic acid and sulfur trioxide.

14. The process of claim 8, wherein said organic acid is a phenylacetic acid, thienylacetic acid, mandelic acid, pyridylmercaptoacetic acid, tetrazoylacetic acid, 1-aminocyclohexanecarboxylic acid, α-aminocyclohexadienylacetic acid, α-aminocyclohexenylacetic acid or cyanoacetic acid.

15. A process for preparing an N-protected-cephalosporin C diester having the formula (III):

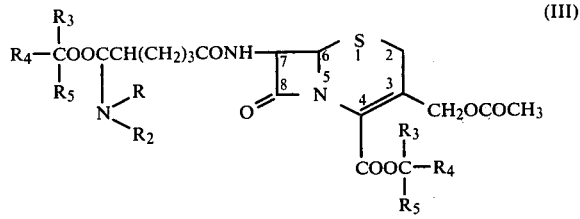

(III)

wherein $R_1$ represents a group selected from the group consisting of $C_1$–$C_4$ alkanoyl; benzoyl; nitrobenzoyl; halobenzoyl; $C_1$–$C_5$ alkoxycarbonyl; $C_1$–$C_4$ haloalkoxycarbonyl; ($C_1$–$C_4$)alkoxy-($C_1$–$C_4$)alkoxycarbonyl; benzyloxycarbonyl; $C_1$–$C_2$ alkoxybenzyloxycarbonyl; halobenzyloxycarbonyl; phenyl substituted with nitro, methoxy, cyano or carbomethoxy; benzene sulfonyl; tosyl and nitrophenylsulfenyl; $R_2$ is hydrogen, or together with $R_1$ forms a ring selected from the group consisting of phthaloyl and halophthaloyl; $R_3$, $R_4$ and $R_5$ may be the same or different, each represents a hydrogen atom, alkyl having from 1 to 4 carbon atoms, phenyl, nitrophenyl, methoxyphenyl, benzoyl, benzyloxy, benzylthio, ($C_1$–$C_4$)alkanoyloxy, benzoxy or benzoyloxy,
which comprises contacting an N-protected-cephalosporin C having the formula (I):

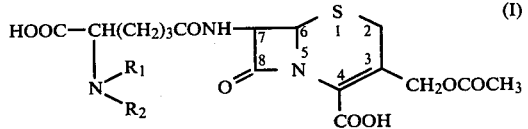

(I)

wherein $R_1$ and $R_2$ are as defined above,
in liquid sulfur dioxide in the presence of a secondary amine or a tertiary amine selected from the group consisting of diethylamine, monomethylaniline, piperidine, pyrrolidine, N,N'-tetramethylguanidine, triethylamine, tripropylamine, tributylamine, pyridine, picoline, lutidine, collidine, quinoline, isoquinoline, N-methylmorpholine, N-ethylmorpholine, N-methylpiperidine, N-ethylpiperidine, N-methylpyrrolidine, N-ethylpyrrolidine, N,N-dimethylaniline and N,N-diethylaniline, at a temperature of from about $-10°$ C. to about $-5°$ C. with an esterifying agent having the formula (II):

(II)

wherein $R_3$, $R_4$ and $R_5$ are as defined above, and X represents a chlorine atom, a bromine atom, an iodine atom, methanesulfonyloxy, benzenesulfonyloxy or p-toluenesulfonyloxy.

16. The process of claim 15, wherein the group

of said diester (III) represents t-butyl, p-nitrophenylmethyl, benzhydryl, di-(p-nitro)benzhydryl, di-(p-methoxy)benzhydryl, benzyloxymethyl, benzylthiomethyl, phenacyl, acetoxymethyl, pivaloyloxymethyl, benzoxymethyl, or α-benzoyloxyethyl.

* * * * *